United States Patent [19]

Uneme et al.

[11] Patent Number: 6,008,363

[45] Date of Patent: Dec. 28, 1999

[54] PROCESS FOR PRODUCING GUANIDINE DERIVATIVES, INTERMEDIATES THEREFOR AND THEIR PRODUCTION

[75] Inventors: Hideki Uneme; Masato Konobe; Hitoshi Ishizuka; Yasuo Kamiya, all of Ibaraki, Japan

[73] Assignee: Takeda Chemical Industries, Ltd., Osaka, Japan

[21] Appl. No.: 08/793,097

[22] PCT Filed: Jun. 19, 1996

[86] PCT No.: PCT/JP96/01694

§ 371 Date: Feb. 21, 1997

§ 102(e) Date: Feb. 21, 1997

[87] PCT Pub. No.: WO97/00867

PCT Pub. Date: Jan. 9, 1997

[30] Foreign Application Priority Data

Jun. 23, 1995 [JP] Japan .................................... 7-158199
Nov. 17, 1995 [JP] Japan .................................... 7-300278

[51] Int. Cl.$^6$ ...................... C07C 277/08; C07C 279/36; C07C 273/18; C07D 277/28; C07D 213/38; C07D 209/48

[52] U.S. Cl. .......................... 546/334; 546/329; 548/203; 548/205; 558/8

[58] Field of Search ............................ 558/8, 9; 546/329, 546/334; 548/203, 205

[56] References Cited

U.S. PATENT DOCUMENTS

| | | | |
|---|---|---|---|
| 5,034,404 | 7/1991 | Uneme et al. | 514/365 |
| 5,180,833 | 1/1993 | Uneme et al. | 548/202 |
| 5,214,152 | 5/1993 | Minamida et al. | 548/181 |
| 5,489,603 | 2/1996 | Uneme et al. | 514/365 |

FOREIGN PATENT DOCUMENTS

| | | |
|---|---|---|
| 0302389 | 2/1989 | European Pat. Off. . |
| 0 375 907 | 7/1990 | European Pat. Off. . |
| 0 376 279 | 7/1990 | European Pat. Off. . |
| 0 452 782 | 10/1991 | European Pat. Off. . |
| 0471372 | 2/1992 | European Pat. Off. . |
| 4021674 | 1/1992 | Japan . |
| 10120666 | 5/1998 | Japan . |
| WO 97/00867 | 1/1997 | WIPO . |

OTHER PUBLICATIONS

Heyboer et al, Rec, Trav. Chim., vol. 81, pp. 69 to 72, 1962.

*Primary Examiner*—Floyd D. Higel
*Attorney, Agent, or Firm*—Foley & Lardner

[57] ABSTRACT

A process for producing the compound [I] or a salt thereof having excellent pesticidal activity as shown in the following schema.

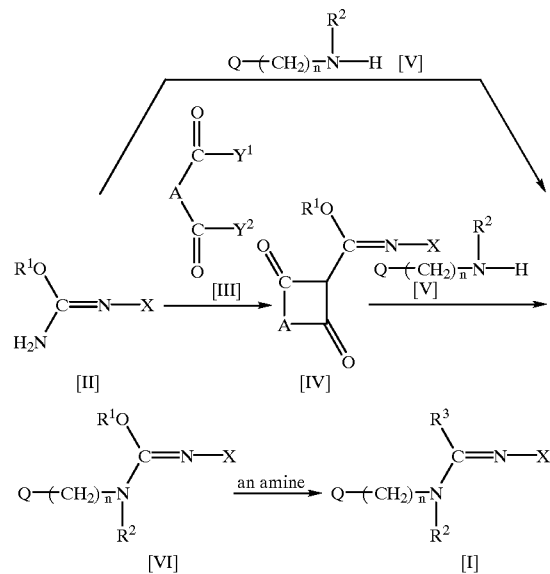

13 Claims, No Drawings

PROCESS FOR PRODUCING GUANIDINE DERIVATIVES, INTERMEDIATES THEREFOR AND THEIR PRODUCTION

This application is a §371 national phase of PCT/JP96/01694, filed Jun. 19, 1996.

TECHNICAL FIELD

The present invention relates to a process for producing guanidine derivatives which are useful as insecticides, novel intermediates therefor, and a process for producing the intermediates.

BACKGROUND ART

EP-A 376279 corresponding to JP-A H3(1991)-157308, for instance, describes guanidine derivatives having pesticidal activity and a process for producing the derivatives. Moreover, as an improved production process for the guanidine derivatives, EP-A 452782 corresponding to JP-A H5(1993)-9173 discloses a production process via an isothiourea derivative having a cyclic diacyl group as shown in the following schema 1.

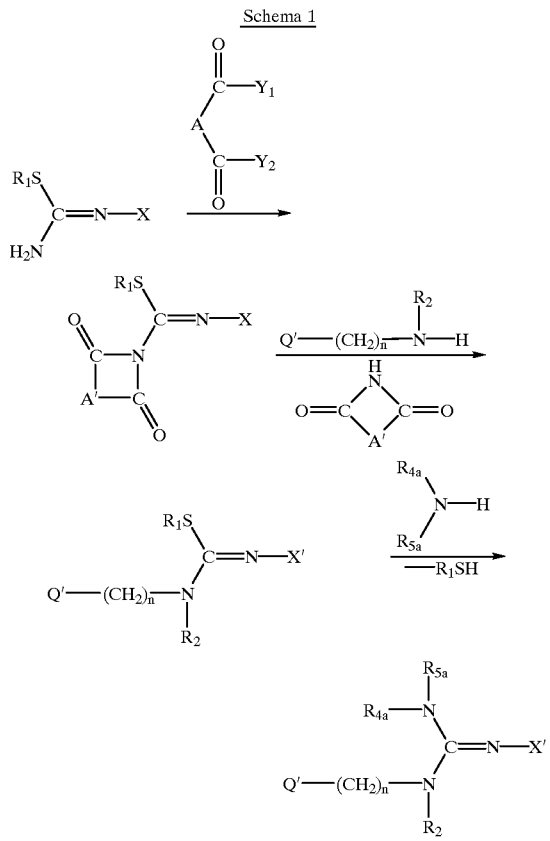

wherein $R_1$, $R_2$, $R_{4a}$, and $R_{5a}$ are the same or different, H or a hydrocarbon group which may optionally be substituted; A' is a divalent hydrocarbon group which may optionally be substituted; Q' is a heterocyclic group which may optionally be substituted; X' is an electron withdrawing group; $Y_1$ and $Y_2$ are the same or different, a leaving group; n is 0 or 1.

Furthermore, EP-A 375907 corresponding to JP-A H2(1990)-288860 discloses guanidine derivatives having pesticidal activity, and the following process for producing the derivatives.

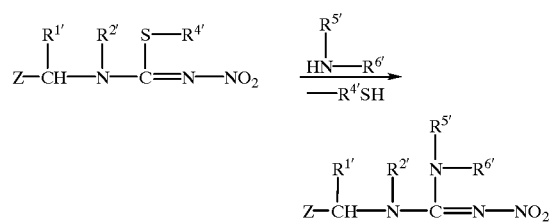

wherein $R^{1'}$ and $R^{2'}$ are hydrogen or $C_{1-4}$ alkyl, $R^{4'}$ is $C_{1-4}$ alkyl, Z is a five- or six-membered heterocyclic group having at least one nitrogen atom which may be substituted by halegen or $C_{1-4}$ alkyl, $R^{5'}$ and $R^{6'}$ are hydrogen or $C_{1-4}$ alkyl.

However, in these processes for producing the guanidine derivatives, there are some problems such that a mercaptan compound of RSH (wherein R is a hydrocarbon group which may optionally be substituted) having bad smell is formed as a by-product.

In the above state of the art, the object of present invention is to provide a process which is advantageous to an industrial mass production of guanidine derivatives in a higher yield by simple and convenient reaction procedures without bad smell, novel intermediates therefor, and a process for producing the intermediates.

DISCLOSURE OF INVENTION

To accomplish the above-mentioned object, the inventors of the present invention earnestly explored for a new production route to a guanidine derivative of the formula [I]:

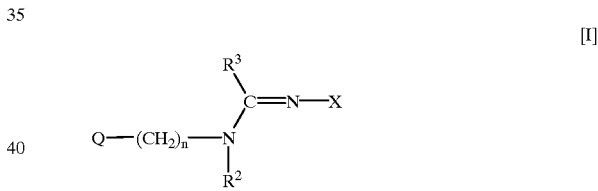

wherein $R^2$ is H or a hydrocarbon group which may optionally be substituted; $R^3$ is an amino group which may optionally be substituted; Q is a heterocyclic group which may optionally be substituted; X is an electron attracting group; n is 0 or 1.

As a result, the inventors discovered that an N-cyclodiacyl-N'-substituted isourea derivative of the formula [IV]:

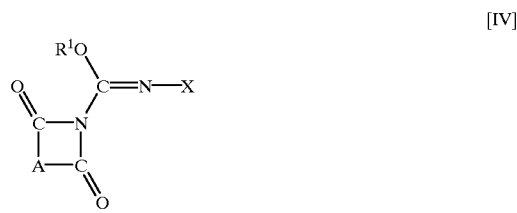

wherein $R^1$ is a hydrocarbon group which may optionally be substituted, A is a divalent hydrocarbon group which may optionally be substituted, and X is as defined above, can be produced in high yield by reacting an N-substituted isourea derivative of the formula [II]:

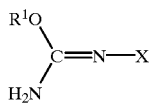

wherein the symbols are as defined above, or a salt thereof, with a compound of the formula [III]:

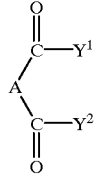

wherein $Y^1$ and $Y^2$ are the same or different, a leaving group; A is as defined above.

The inventors further found that a compound of the formula [VI]:

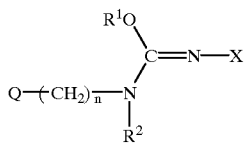

wherein the symbols are as defined above, or a salt thereof, can be produced in high yield by reacting the compound [IV] with a compound of the formula [V]:

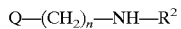

wherein the symbols are as defined above, or a salt thereof.

Based on the above findings, the inventors did further research and found surprisingly that when the compound [VI] or a salt thereof is reacted with an amine or a salt thereof either in water or in a mixture of water and an organic solvent, the guanidine derivative [I] or a salt thereof is produced in high yield.

And, the inventors further found that the compound [VI] or a salt thereof can be produced by reacting the compound [II] or a salt thereof with the compound [V] or a salt thereof not via the compound [IV]. The inventors did further reseach and discovered to their own surprise that the compound [VI] or a salt thereof can be produced in a further improved yield by conducting the above reaction in the presence of an acid either in water or in a mixture of water and an organic solvent.

Based on these findings, the inventors have conducted further study to accomplish the present invention.

The present invention, therefore, is directed to:
(1) a process for producing a compound of the formula [VI]:

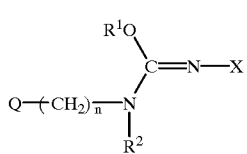

wherein $R^1$ is a hydrocarbon group which may optionally be substituted, $R^2$ is H or a hydrocarbon group which may optionally be substituted, Q is a heterocyclic group which may optionally be substituted, X is an electron attracting group, and n is 0 or 1, or a salt thereof, which comprises
(A) reacting a compound of the formula [II]:

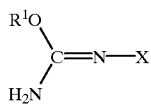

wherein the symbols are as defined above, or a salt thereof, with a compound of the formula [V]:

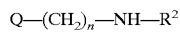

wherein the symbols are as defined above, or a salt thereof, or
(B) reacting the compound [II] or a salt thereof with a compound of the formula [III]:

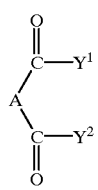

wherein A is a divalent hydrocarbon group which may optionally be substituted, and $Y^1$ and $Y^2$ are the same or different, a leaving group, and further reacting the resultant compound of the formula [IV]:

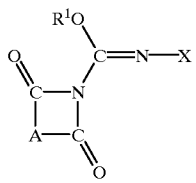

wherein the symbols are as defined above, with the compound [V] or a salt thereof,
(2) a process according to (1), wherein $R^1$ is a $C_{1-3}$ alkyl group,
(3) a process according to (1), wherein X is nitro,
(4) a process according to (1), wherein $R^2$ is H or a $C_{1-4}$ alkyl group,
(5) a process according to (1), wherein Q is a 5- or 6-membered aromatic heterocyclic group, having at least one nitrogen atom or sulfur atom, which may optionally be halogenated, (6) a process according to (1), wherein n is 1, (7) a process according to (1), wherein the reaction in process (A) is conducted in water or in a mixture of water and an organic solvent, (8) a process according to (1), wherein the reaction in process (A) is conducted in the range of about pH 5 to pH 8, (9) a process for producing a compound of the formula:

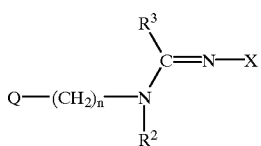

[I]

wherein $R^3$ is an amino group which may optionally be substituted, and $R^2$, Q, X and n are as defined above, or a salt thereof, which comprises (i) (A) reacting the compound of the formula [II] or a salt thereof, with the compound of the formula [V] or a salt thereof, or (B) reacting the compound of the formula [II] or a salt thereof, with the compound of the formula [III], and further reacting the resultant compound of the formula [IV], with the compound of the formula [V] or a salt thereof, and further (ii) reacting the resultant compound of the formula [VI] or a salt thereof, with an amine compound or a salt thereof,

(10) a process for producing O-methyl-N-(6-chloro-3-pyridylmethyl)-N'-nitroisourea or a salt thereof, which comprises reacting O-methyl-N-nitroisourea or a salt thereof with 5-(aminomethyl)-2-chloropyridine or a salt thereof,

(11) a process for producing O-methyl-N-(2-chloro-5-thiazolylmethyl)-N'-nitroisourea or a salt thereof, which comprises reacting O-methyl-N-nitroisourea or a salt thereof with 5-(aminomethyl)-2-chlorothiazole or a salt thereof,

(12) the compound of the formula [IV],

(13) a compound according to (12), wherein $R^1$ is a $C_{1-3}$ alkyl group,

(14) a compound according to (12), wherein A is a $C_{6-14}$ arylene group,

(15) a compound according to (12), wherein X is nitro,

(16) a compound according to (12), which is O-methyl-N-nitro-N'-phthaloylisourea,

(17) a process for producing the compound [IV], which comprises reacting the compound [II] or a salt thereof, with the compound [III],

(18) a process for producing the compound [VI] or a salt thereof, which comprises reacting the compound [IV], with the compound [V] or a salt thereof,

(19) a process according to (9), wherein the reaction is conducted in water or in a mixture of water and an organic solvent,

(20) a process according to (9), wherein the amine compound is represented by the formula:

$R^4R^5NH$ wherein $R^4$ and $R^5$ are the same or different, H or a hydrocarbon group which may optionally be substituted, or both $R^4$ and $R^5$ are combined with the adjacent nitrogen atom to form a cyclic amino group,

(21) a process according to (9), wherein the amine compound is a $C_{1-4}$ alkylamine,

(22) a process for producing 1-(6-chloro-3-pyridylmethyl)-3-methyl-2-nitroguanidine or a salt thereof, which comprises reacting O-methyl-N-(6-chloro-3-pyridylmethyl)-N'-nitroisourea or a salt thereof, with methylamine or a salt thereof in water or in a mixture of water and an organic solvent, and

(23) a process for producing 1-(2-chloro-5-thiazolylmethyl)-3-methyl-2-nitroguanidine or a salt thereof, which comprises reacting O-methyl-N-(2-chloro-5-thiazolylmethyl)-N'-nitroisourea or a salt thereof, with methylamine or a salt thereof in water or in a mixture of water and an organic solvent.

The hydrocarbon group of the hydrocarbon group which may optionally be substituted for $R^1$ and $R^2$ includes saturated and unsaturated aliphatic hydrocarbon groups and aromatic hydrocarbon groups. The preferred saturated or unsaturated aliphatic hydrocarbon groups are $C_{1-15}$ alkyl groups such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl and pentadecyl, $C_{2-10}$ alkenyl groups such as vinyl, allyl, 2-methylallyl, 2-butenyl, 3-butenyl and 3-octenyl, $C_{2-10}$ alkynyl groups such as ethynyl, 2-propynyl and 3-hexynyl, $C_{3-10}$ cycloalkyl groups such as cyclopropyl, cyclobutyl, cyclopentyl and cyclohexyl, and $C_{3-10}$ cycloalkenyl groups such as cyclopropenyl, cyclopentenyl and cyclohexenyl. The preferred aromatic hydrocarbon groups are $C_{6-14}$ aryl groups such as phenyl, naphthyl, azulenyl, anthryl and phenanthryl, and $C_{7-11}$ aralkyl groups such as benzyl and phenylethyl.

The heterocyclic group of the heterocyclic group which may optionally be substituted for Q includes 3- to 8-membered heterocyclic groups containing 1 to 5 heteroatoms selected from oxygen, sulfur and nitrogen, and fused heterocyclic groups thereof, such as 2- or 3-thienyl, 2- or 3-furyl, 1-, 2- or 3-pyrrolyl, 2-, 3- or 4-pyridyl, 2-, 4- or 5-oxazolyl, 2-, 4- or 5-thiazolyl, 1-, 3-, 4- or 5-pyrazolyl, 1-, 2-, 4- or 5-imidazolyl, 3-, 4- or 5-isoxazolyl, 3-, 4- or 5-isothiazolyl, 3- or 5-(1,2,4-oxadiazolyl), 2- or 5-(1,3,4-oxadiazolyl), 3- or 5-(1,2,4-thiadiazolyl), 2- or 5-(1,3,4-thiadiazolyl), 4- or 5-(1,2,3-thiadiazolyl), 3- or 4-(1,2,5-thiadiazolyl), 1-, 4- or 5-(1,2,3-triazolyl), 1-, 3- or 5-(1,2,4-triazolyl), 1- or 5-(1H-tetrazolyl), 2- or 5-(2H-tetrazolyl), N-oxide-2-, 3- or 4-pyridyl, 2-, 4- or 5-pyrimidinyl, N-oxide-2-, 4- or 5-pyrimidinyl, 3- or 4-pyridazinyl, pyrazinyl, N-oxide-3- or 4-pyridazinyl, indolyl, benzofuryl, benzothiazolyl, benzoxazolyl, triazinyl, oxotriazinyl, imidazo[1,2-a]pyridinyl, tetrazolo[1,5-b]pyridazinyl, triazolo[4,5-b]pyridazinyl, oxoimidazinyl, dioxotriazinyl, chromanyl, benzoimidazolyl, quinolyl, isoquinolyl, cinnolyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, phenoxazinyl, aziridinyl, azetidinyl, pyrrolinyl, pyrrolidinyl, piperidinyl, piperidino, pyranyl, thiopyranyl, 1,4-dioxanyl, morpholinyl, morpholino, 1,4-thiazinyl, 1,3-thiazinyl, piperazinyl and piperazino.

Each of the above-mentioned hydrocarbon groups and heterocyclic groups may have the same or different 1 to 5 substituents, preferably 1 to 3 substituents, in substitutable positions. Moreover, in regard of halogen, each hydrocarbon or heterocyclic group may optionally be substituted with up to the maximum possible number of halogen atoms. The preferred substituent includes $C_{1-15}$ alkyl groups such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl and pentadecyl, $C_{3-10}$ cycloalkyl groups such as cyclopropyl, cyclobutyl, cyclopentyl and cyclohexyl, $C_{2-10}$ alkenyl groups such as vinyl, allyl, 2-methylallyl, 2-butenyl, 3-butenyl and 3-octenyl, $C_{2-10}$ alkynyl groups such as ethynyl, 2-propynyl and 3-hexynyl, $C_{3-10}$ cycloalkenyl groups such as cyclopropenyl, cyclopentenyl and cyclohexenyl, $C_{6-10}$ aryl groups such as phenyl and naphthyl, $C_{7-11}$ aralkyl groups such as benzyl and phenylethyl, nitro, nitroso, hydroxyl, mercapto, cyano, oxo, thioxo, carbamoyl, mono- or di-$C_{1-6}$ alkyl-carbamoyl groups such as methylcarbamoyl and dimethylcarbamoyl, $C_{6-14}$ aryl-carbamoyl groups such as phenylcarbamoyl, carboxyl, $C_{1-4}$ alkoxy-carbonyl groups such as methoxycarbonyl and ethoxycarbonyl, $C_{6-14}$ aryloxy-carbonyl such as phenoxycarbonyl, sulfo, halogen such as fluorine, chlorine, bromine and iodine, $C_{1-4}$ alkoxy groups such as methoxy, ethoxy, propoxy, isopropoxy, butoxy, isobutoxy, s-butoxy and t-butoxy, $C_{6-10}$ aryloxy groups such as phenoxy, $C_{1-4}$ alkylthio groups such as methylthio, ethylthio, propylthio, isopropylthio, butylthio, isobutylthio, s-butylthio and t-butylthio, $C_{6-10}$ arylthio groups such as phenylthio, $C_{1-4}$ alkylsulfinyl groups such as methylsulfinyl, ethylsulfinyl, propylsulfinyl, isopropylsulfinyl, butylsulfinyl, isobutylsulfinyl, s-butylsulfinyl and t-butylsulfinyl, $C_{6-10}$ arylsulfinyl groups such as phenylsulfinyl, $C_{1-4}$ alkylsulfonyl groups such as methylsulfonyl, ethylsulfonyl, propylsulfonyl, isopropylsulfonyl, butylsulfonyl, isobutylsulfonyl, s-butylsulfony and t-butylsulfonyl, $C_{6-10}$ arylsulfonyl groups such as phenylsulfonyl, $C_{1-4}$ alkoxysulfonyl groups such as methoxysulfonyl, ethoxysulfonyl, propoxysulfonyl, isopropoxysulfonyl, butoxysulfonyl, isobutyloxysulfonyl, s-butoxysulfonyl and t-butoxysulfonyl, $C_{6-10}$ aryloxysulfonyl groups such as phenoxysulfonyl, amino, $C_{1-11}$ carboxylic acylamino groups such as acetylamino, propionylamino and benzoylamino, mono- or di-$C_{1-4}$ alkylamino groups such as methylamino, ethylamino, propylamino, isopropylamino, butylamino, dimethylamino and diethylamino, $C_{3-6}$ cycloalkylamino groups such as cyclohexylamino, $C_{6-10}$ arylamino groups such as anilino, tri-substituted silyl groups such as trimethylsilyl, t-butyldimethylsilyl, triphenylsilyl and t-butylmethoxyphenylsilyl, $C_{1-11}$ carboxylic acyl groups such as formyl, acetyl and benzoyl, 3- to 6-membered heterocyclic groups containing 1 to 5 hetero-atoms selected from oxygen, sulfur and nitrogen, and fused heterocyclic groups thereof, such as 2- or 3-thienyl, 2- or 3-furyl, 1-, 2- or 3-pyrrolyl, 2-, 3- or 4-pyridyl, 2-, 4- or 5-oxazolyl, 2-, 4- or 5-thiazolyl, 1-, 3-, 4- or 5-pyrazolyl, 1-, 2-, 4- or 5-imidazolyl, 3-, 4- or 5-isoxazolyl, 3-, 4- or 5-isothiazolyl, 1,2,3- or 1,2,4-triazolyl, 2-, 4- or 5-pyrimidinyl, benzothiazolyl, benzoxazolyl, triazinyl, oxiranyl, aziridinyl, pyrrolidinyl, piperidinyl, morpholinyl, benzimidazolyl, quinolyl and isoquinolyl. When two or more substituents are present, two of the substituents may form a divalent group such as $C_{1-6}$ alkylene (e.g. methylene, ethylene, trimethylene, tetramethylene and propenylene), 3-oxapentamethylene, vinylene, benzylidene, methylenedioxy, 2-thiatrimethylene, oxalyl, malonvl, succinyl, maleoyl, phthaloyl, oxygen, sulfur, imino, azo or hydrazo. When any of these substituents is aryl, aralkyl, cycloalkyl, cycloalkenyl aryloxy, arylthio, arylsulfinyl, arylsulfonyl, arylcarbamoyl, aryloxycarbonyl, aryloxysulfonyl, arylamino, cycloalkylamino, carboxylic acyl, carboxylic acylamino, tri-substituted silyl, heterocyclic group or divalent group, it may further have 1 to 5 substituents such as halogen (e.g. fluorine, chlorine, bromine or iodine), hydroxyl, nitro, cyano, $C_{1-4}$ alkyl (e.g. methyl, ethyl, propyl, isopropyl, butyl, isobutyl, s-butyl or t-butyl), $C_{2-4}$ alkenyl (e.g. vinyl or allyl), $C_{2-4}$ alkynyl (e.g. ethynyl or 2-propynyl), phenyl, $C_{1-4}$ alkoxy (e.g. methoxy or ethoxy), phenoxy, $C_{1-4}$ alkylthio (e.g. methylthio or ethylthio) and phenylthio, and particularly in regard of halogen, the above-mentioned substituent may optionally be substituted with up to the maximum possible number of halogen atoms. When any of these substituents is alkyl, alkenyl, alkynyl, alkoxy, alkylthio, alkylsulfinyl, alkylsulfonyl, alkylcarbamoyl, alkoxycarbonyl, alkoxysulfonyl, amino or alkylamino, it may further have 1 to 5 substituents such as halogen mentioned above, hydroxyl, nitro, cyano, $C_{1-4}$ alkoxy and $C_{1-4}$ alkylthio, and particularly in regard of halogen, the above-mentioned substituent may optionally be substituted with the maximum possible number of halogen atoms.

The electron attracting group for X includes nitro, cyano, $C_{1-10}$ carboxylic acyl which may optionally be substituted with 1 to 5 halogen atoms (e.g. fluorine, chlorine, bromine or iodine) such as acetyl, trichloroacetyl, trifluoroacetyl, pentafluoropropionyl or benzoyl, 3- to 6-membered heterocyclic-carbonyl containing 1 to 4 hetero-atoms selected from oxygen, sulfur and nitrogen as ring-constituent atoms such as nicotinoyl, furoyl or thenoyl, carboxyl, $C_{1-4}$ alkoxycarbonyl such as methoxycarbonyl or ethoxycarbonyl, $C_{6-10}$ aryloxy-carbonyl such as phenoxycarbonyl, 3- to 6-membered heterocyclic-oxycarbonyl containing 1 to 4 hetero-atoms selected from oxygen, sulfur and nitrogen as ring-constituent atoms such as pyridyloxycarbonyl or thienyloxycarbonyl, carbamoyl, $C_{1-4}$ alkylsulfonylthiocarbamoyl such as methylsulfonyl-thiocarbamoyl, $C_{1-4}$ alkylsulfonyl which may optionally be substituted with 1 to 5 halogen atoms (e.g. fluorine, chlorine, bromine or iodine) such as methylsulfonyl, ethylsulfonyl or trifluoromethylsulfonyl, sulfamoyl and $C_{1-4}$ dialkoxyphosphoryl such as diethoxyphosphoryl.

The divalent hydrocarbon group of the divalent hydrocarbon group which may optionally be substituted for A includes $C_{2-4}$ alkylene such as ethylene, propylene or trimethylene, $C_{1-4}$ alkenylene such as vinylene or propenylene, $C_{3-10}$ cycloalkylene such as 1,2-cyclopentylene or 1,2-cyclohexylene, $C_{3-10}$ cycloalkenylene such as 1-cyclopropen-1,2-ylene, 1-cyclohexen-1,2-ylene or 4-cyclohexen-1,2-ylene, and $C_{6-10}$ arylene such as O-phenylene. The substituents of this divalent hydrocarbon group may for example be those mentioned as substituents of the hydrocarbon group which may optionally be substituted for $R^1$.

The leaving group for $Y^1$ and $Y^2$ includes halogen (e.g. fluorine, chlorine, bromine, or iodine), $C_{1-4}$ alkylsulfonyloxy which may optionally be substituted with 1 to 3 halogen atoms (e.g. fluorine, chlorine, bromine or iodine) such as methanesulfonyloxy, ethanesulfonyloxy or trifluoromethanesulfonyloxy, $C_{6-10}$ arylsulfonyloxy which may optionally be substituted with 1 to 4 substituents selected from the group consisting of halogen (e.g. fluorine, chlorine, bromine or iodine) and $C_{1-4}$ alkyl (e.g. methyl, ethyl) such as benzenesulfonyloxy, p-bromobenzenesulfonyloxy or mesitylenesulfonyloxy, $C_{1-6}$ carboxylic acyloxy which may optionally be substituted with 1 to 3 halogen atoms (e.g. fluorine, chlorine, bromine or iodine) such as acetyloxy or trifluoroacetyloxy, $C_{6-10}$ aryl-carbonyloxy (e.g. benzoyloxy), $C_{1-4}$ alkylthio (e.g.

methylthio or ethylthio), $C_{6-10}$ arylthio which may optionally be substituted with 1 to 5 halogen atoms (e.g. fluorine, chlorine, bromine or iodine) such as phenylthio or pentachlorophenylthio, and 3- to 6-membered heterocyclic-thio containing 1 to 4 hetero-atoms selected from oxygen, sulfur and nitrogen as ring-constituent atoms (e.g. 2-pyridylthio or 2-benzothiazolylthio). Furthermore, $Y^1$ and $Y^2$ may jointly represent an oxygen atom or a sulfur atom.

The amine compound mentioned above may for example be ammonia, a primary amine or a secondary amine, which are represented by the formula:

$$R^4R^5NH$$

wherein $R^4$ and $R^5$ are the same or different, H or a hydrocarbon group which may optionally be substituted; or both $R^4$ and $R^5$ are combined with the adjacent nitrogen atom to form a cyclic amino group.

The hydrocarbon group which may optionally be substituted for $R^4$ and $R^5$ may for example be those mentioned as the hydrocarbon group which may optionally be substituted for $R^1$ and $R^2$ including substituents thereof. The cyclic amino group which $R^4$ and $R^5$ may form together with the adjacent nitrogen atom includes aziridino, azetidino, pyrrolidino, morpholino and thiomorpholino.

The amino group which may optionally be substituted for $R^3$ includes amino, secondary amino, which are represented by the formula:

$$R^4R^5N—$$

wherein $R^4$ and $R^5$ are as defined above.

$R^1$ is preferably a saturated or unsaturated aliphatic hydrocarbon group and more preferably a $C_{1-15}$ alkyl group. Particularly preferred are $C_{1-3}$ alkyl groups, methyl being most preferred.

$R^2$ is preferably H or a saturated or unsaturated aliphatic hydrocarbon group. Particularly preferred are H and $C_{1-15}$ alkyl. Still more preferred are H and $C_{1-4}$ alkyl, H being most preferred.

$R^3$ is preferably a secondary amino group and more preferably a $C_{1-4}$ alkylamino group. Methylamino is most preferred.

The amine compound is preferably a primary amine, more preferably a $C_{1-4}$ alkylamine. Methylamine is most preferred.

A is preferably $C_{1-4}$ alkylene, $C_{2-4}$ alkenylene and $C_{6-14}$ arylene, more preferably $C_{6-14}$ arylene. Particularly preferred are ethylene, trimethylene, vinylene and O-phenylene, O-phenylene being most preferred.

Q is preferably a 5 or 6-membered aromatic heterocyclic group containing at least one nitrogen or sulfur atom as a ring-constituent atom, which may optionally be halogenated. Particularly preferred are halogenated pyridyl and halogenated thiazolyl. Specifically, 6-chloro-3-pyridyl and 2-chloro-5-thiazolyl are most preferred.

n is preferably 1.

X is preferably nitro or cyano, nitro being particularly preferred.

$Y^1$ and $Y^2$ are preferably both halogen as mentioned above, more preferably chlorine.

The salts of guanidine derivative [I], compound [II], compound [V], compound [VI] and amine compound mentioned above can be any agrochemically acceptable salts, typically salts with various inorganic acids such as hydrochloric acid, hydrobromic acid, hydroiodic acid, phosphoric acid, sulfuric acid and perchloric acid, and salts with various organic acids such as formic acid, acetic acid, tartaric acid, malic acid, citric acid, oxalic acid, succinic acid, benzoic acid, picric acid, methanesulfonic acid and p-toluenesulfonic acid. When any of said guanidine derivative [I], compounds [II], [V] and [VI] and amine compound has an acidic group such as carboxyl, it may form a salt with a base. The base which can be used includes inorganic bases such as sodium, potassium, lithium, calcium, magnesium and ammonia, and organic bases such as pyridine, collidine, dimethylamine, triethylamine and triethanolamine.

When compound [III] or [IV] has a basic group such as amino, it may form salts with inorganic and organic acids such as those mentioned just above. Moreover, when compound [III] or [IV] has an acidic group such as carboxyl, it may form salts with inorganic and organic bases such as those mentioned just above.

The process of the present invention can be carried out under the conditions described hereinafter. In case the reaction product obtained is a free compound, it can be converted into the salts such as those mentioned above and conversely in case the reaction product is a salt, it can be converted into a free compound, by the known procedure in either case. Furthermore, when the starting compound may form a salt such as those mentioned above, it can be used not only in the free form but also in the form of a salt. Therefore, the following descriptions of starting compounds and reaction products should be construed to cover both the free compounds and salts (e.g. salts with the acids or bases mentioned for guanidine derivative [I]).

(A) Compound [II] is reacted with compound [III] to give compound [IV].

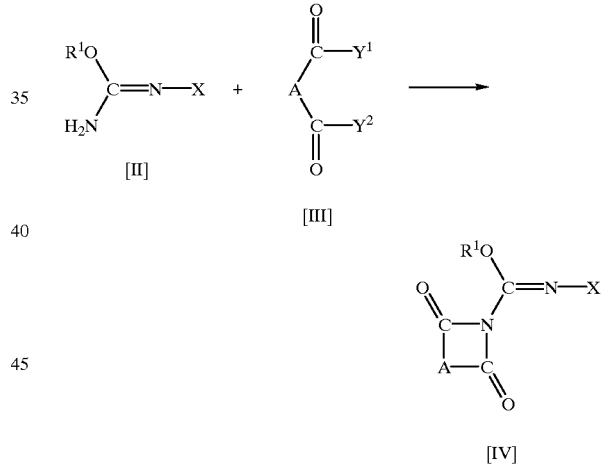

(In the above reaction schema, all symbols are as defined above)

With respect to compound [II], compound [III] is used in a proportion of about 0.8 to 5 equivalents, preferably about 1 to 1.5 equivalents, but it can be used in large excess unless it is detrimental to the reaction.

This reaction can be carried out advantageously in the presence of a base. The base includes various inorganic bases such as alkali metal hydrogen carbonates (e.g. sodium hydrogen carbonate and potassium hydrogen carbonate), alkali metal carbonates (e.g. sodium carbonate and potassium carbonate), alkali metal hydroxides (e.g. sodium hydroxide, potassium hydroxide), alkaline earth metal hydroxides (e.g. calcium hydroxide), alkyllithium (e.g. butyllithium), aryllithium (e.g. phenyllithium), alkali metal amides (e.g. sodium amide and lithium diisopropylamide), alkali metal hydrides (e.g. sodium hydride and potassium hydride), alkali metal alkoxides (e.g. sodium methoxide and sodium ethoxide), alkali metals (e.g. sodium metal and potassium metal), and various organic bases such as triethylamine, tributylamine, N,N-dimethylaniline, pyridine, picoline, lutidine, collidine, 5-ethyl-2-methylpyridine, 4-(dimethylamino)pyridine and 1,8-diazabicyclo[5.4.0] undecene-7 (hereinafter abbreviated as DBU). The above organic bases can be used as solvents as well. With respect to compound [III], the base is used in a proportion of about 0.5 to 20 equivalents, preferably about 1.8 to 4 equivalents.

While the reaction can be conducted in the absence of a solvent, it is usually carried out in a solvent which does not interfere with the reaction. The solvent includes aromatic hydrocarbons such as benzene, toluene and xylene, halogenated hydrocarbons such as dichloromethane, chloroform, 1,2-dichloroethane and carbon tetrachloride, saturated hydrocarbons such as hexane, heptane and cyclohexane, ethers such as diethyl ether, tetrahydrofuran (hereinafter abbreviated as THF) and dioxane, ketones such as acetone and methyl ethyl ketone, nitriles such as acetonitrile and propionitrile, sulfoxides such as dimethyl sulfoxide (hereinafter abbreviated as DMSO), acid amides such as N,N-dimethylformamide (hereinafter abbreviated as DMF) and N,N-dimethylacetamide, esters such as ethyl acetate and butyl acetate, alcohols such as methanol, ethanol, propanol and isopropyl alcohol, and water. These solvents can be used independently or, where needed, as an appropriate mixture of two or more species, for example in a ratio of about 1:1 to 1:10 (by volume). Where the reaction system is not homogeneous, the reaction may be conducted in the presence of a phase transfer catalyst such as quaternary ammonium salts, (e.g. triethylbenzylammonium chloride, tri-n-octylmethylammonium chloride, trimethyldecylammonium chloride, tetramethylammonium bromide and cetylpyridinium bromide) and crown ethers.

The reaction temperature is usually in the range of about −20 to 250° C., preferably about −10 to 50° C. The reaction time is usually in the range of about 10 minutes to 50 hours, preferably about 10 minutes to 10 hours.

In this reaction step, it is sometimes advantageous to add a lower alcohol having 1 to 4 carbon atoms such as methanol and ethanol after the reaction to decompose the residual compound [III] to the corresponding ester compound, facilitating the work-up procedure and leading to an improved purity of compound [IV]. The particularly preferred lower alcohol is methanol. The preferred proportion of such lower alcohol is about 0.1 to 5.0 equivalents with respect to compound [III]. The preferred decomposition time is in the range of about 10 minutes to 5 hours. The preferred decomposition temperature is in the range of about 0 to 50° C.

(B) Compound [IV] is reacted with compound [V] to give compound [VI].

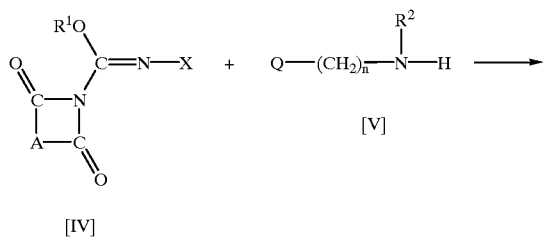

[IV]  [V]

-continued

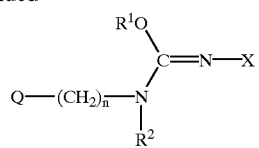

[VI]

(In the reaction schema, all symbols are as defined above)

With respect to compound [IV], compound [V] is used in a proportion of about 0.8 to 5 equivalents, preferably about 1 to 1.5 equivalents, although it can be used in large excess unless it is detrimental to the reaction.

While this reaction is usually conducted in the absence of a base, there are cases in which the reaction proceeds more efficiently in the presence of a base such as those mentioned for process (A).

This reaction is generally conducted in a solvent which does not adversely affect the reaction. The solvent includes the solvents mentioned for process (A). When the reaction system is not homogeneous, a phase transfer catalyst such as those mentioned for process (A) can be employed.

The reaction temperature is usually in the range of about −20 to 200° C., preferably about −10 to 50° C. The reaction time is usually in the range of about 10 minutes to 50 hours, preferably about 10 minutes to 10 hours.

In this reaction, a cyclic imide compound of the following formula [VII]:

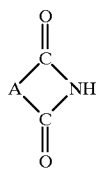

[VII]

wherein A is as defined above, is formed as a by-product. In many cases this compound [VII] can be separated by means of a known technique such as the method utilizing a difference in solubility in a solvent or column chromatography. An alternative procedure (1) applicable to certain cases comprises dissolving the reaction mixture in a basic aqueous medium and neutralizing the solution with an acid gradually for sequential precipitation of compound [VI] and compound [VII]. A further alternative procedure (2) comprises stirring the reaction mixture in a basic aqueous medium at about 0 to 50° C. for about 0.5 to 5 hours to decompose compound [VII] to a hardly precipitatable substance (e.g. dicarboxylic acid monoamide) and neutralizing the system with an acid to precipitate compound [VI]. The base that can be used for these separation procedures typically includes the bases mentioned for process (A) and the acid that can be used typically includes the acids mentioned for conversion of guanidine derivative [I] and other compounds to salts.

(C) Compound [II] is also reacted with compound [V] to give compound [VI].

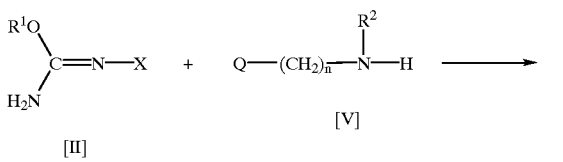

[II]    [V]

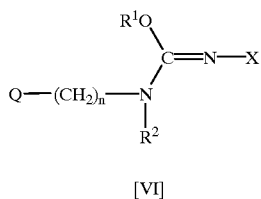

[VI]

(In the above reaction schema, all symbols are as defined above)

With respect to compound [II], compound [V] is used in a proportion of about 0.2 to 5 equivalents, preferably about 0.7 to 1.5 equivalents, but it can be used in large excess unless it is detrimental to the reaction.

This reaction can be carried out efficiently in the range of about pH 5 to pH 8. The reaction is preferably conducted in the presence of an acidic substance to be carried out in such range of pH. The acidic substance includes inorganic acids such as hydrochloric acid, hydrobromic acid, hydroiodic acid, phosphoric acid, sulfuric acid, perchloric acid and nitric acid, and organic acids such as formic acid, acetic acid, tartaric acid, malic acid, citric acid, oxalic acid, succinic acid, benzoic acid, picric acid, methanesulfonic acid and p-toluenesulfonic acid. With respect to compound [II], the acidic substance is used in a proportion of about 0.5 to 10 equivalents and preferably about 0.1 to 2 equivalents.

While the reaction can be conducted in the absence of a solvent, it is usually carried out in a solvent such as those mentioned for process (A). When the reaction system is not homogeneous, a phase transfer catalyst such as those mentioned for process (A) can be employed.

Compound [VI] can be produced in particularly good yield by conducting the above reaction either in water or in a mixture of water and an organic solvent such as those mentioned above. In some instances, the yield can be further increased by adding a salt to the reaction system. The salt includes salts of the acids mentioned above with an alkali metal (e.g. sodium and potassium), an alkaline earth metal (e.g. magnesium and calcium), a metal (e.g. copper, iron and zinc), or ammonia. In certain instances, the reaction can be conducted in a buffer solution (e.g. phosphate buffer).

The reaction temperature is usually in the range of about $-20$ to $250°$ C., preferably about $-10$ to $50°$ C. The reaction time is usually in the range of about 10 minutes to 50 hours, preferably about 1 hour to 20 hours.

(D) Compound [VI] is reacted with an amine compound to give guanidine derivative [I].

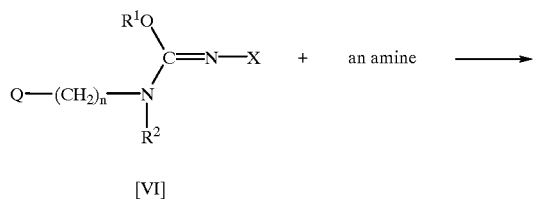

[VI]

-continued

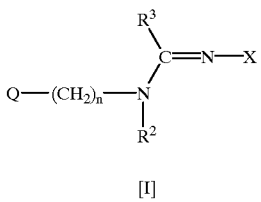

[I]

(In the above reaction schema, all symbols are as defined above)

The amine compound means the same compound as mentioned above.

With respect to compound [VI], the amine compound is used in a proportion of about 0.8 to 10 equivalents, preferably about 1 to 4 equivalents but can be used in large excess unless it is detrimental to the reaction.

In some cases, this reaction may proceed more efficiently in the presence of a base such as those mentioned for process (A), but can be usually carried out without a base.

The reaction is usually carried out in a solvent such as those mentioned for process (A). When the reaction system is not homogeneous, a phase transfer catalyst such as those mentioned for process (A) can be employed. The guanidine derivative [I] can be obtained in high yield particularly when the reaction is conducted in water or a mixture of water with an organic solvent such as those mentioned above. The particularly preferred organic solvent for use in such a solvent mixture includes said halogenated hydrocarbons such as dichloromethane, chloroform and 1,2-dichloroethane.

The reaction temperature is usually in the range of about $-20$ to $200°$ C., preferably about $-10$ to $50°$ C. The reaction time is usually in the range of about 10 minutes to 50 hours, preferably about 10 minutes to 10 hours.

As for the starting compound [VI] for this reaction, the compound which is synthesized by the above process (B) or (C) or any reaction analogous therewith and then isolated can be used, but, the reaction mixture containing compound [VI] so synthesized can also be availabe. Thus, a typical procedure without isolating compound [VI] (1) comprises conducting the above process (B) or (C) either in water or in a mixture of water and an organic solvent (e.g. the organic solvents mentioned above) and, then, adding the amine compound. An alternative procedure (2) comprises conducting the reaction according to the above process (B) or (C) in an organic solvent, adding water to the reaction mixture to prepare a binary phase, and adding the amine compound for reaction. In the latter procedure (2), the by-product compound [VII] may separate out after the first-stage reaction and this by-product may be filtered off but, of course, the process can be further continued without removing the by-product.

The resulting compound [IV], compound [VI] and guanidine derivative [I], as well as their salts, can be respectively isolated and purified by known procedures such as concentration, concentration under reduced pressure, distillation, fractional distillation, solvent extraction, change of pH, redistribution, chromatography, crystallization and recrystallization.

Each of the guanidine derivative [I], compounds [II], [IV] and [VI], and their salts forms cis- and trans-isomers with respect to the position of X and each of the guanidine derivative [I] and compounds [II] and [VI] may theoretically form tautomers depending on its substituent groups. All of these isomers are included in the corresponding guanidine derivative [I], compounds [II], [IV] and [VI], and their salts.

Some species of the compound [II] or a salt thereof which is used as a starting compound in the present invention are known compounds [cf. Rec. Trav. Chim., 81, 69 (1962) for instance]. When X represents nitro, the compound [II] or a salt thereof can be produced by N-nitrating an isourea derivative [VIII] or a salt thereof as shown in the following reaction schema.

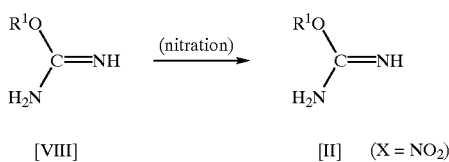

[VIII]    [II] (X = NO$_2$)

(wherein R$^1$ is as defined above)

The commonest nitrating agent is 60 to 100% nitric acid. However, an alkali metal nitrate such as sodium nitrate and potassium nitrate, an alkyl nitrate such as ethyl nitrate and amyl nitrate, nitronium tetrafluoroborate (NO$_2$BF$_4$), nitronium trifluoromethanesulfonate (NO$_2$CF$_3$SO$_3$), or the like can be employed. With respect to compound [VIII], the nitrating agent can be used in a proportion of about 1.0 to 20 equivalents and, taking nitric acid as an example, the preferred proportion is about 1.5 to 10 equivalents.

This reaction can be conducted in the absence of a solvent but is generally carried out in a solvent such as sulfuric acid, acetic acid, acetic anhydride, trifluoroacetic anhydride and trifluoromethanesulfonic acid. In certain cases, the solvents mentioned for process (A) or a mixture thereof can be employed. The particularly preferred solvent is sulfuric acid.

The reaction temperature is usually in the range of about −50 to 100° C., preferably about −20 to 30° C. The reaction time is usually in the range of about 10 minutes to 10 hours, preferably about 30 minutes to 3 hours.

Compound [III] is commercially available or it can be produced by processes known per se or any reactions analogous therewith. Typical processes are described in The Chemistry of Acid Derivatives, Part 1, John Willey & Sons (1979), Chapter 7; The Chemistry of Acid Derivatives, Part 2, John Willey & Sons (1979), Chapter 11; and The Chemistry of AcylHalides, John Willey & Sons (1972), Chapter 2.

Compound [V] or a salt thereof can be produced by processes known per se or any reactions analogous therewith. Typical such processes are described in Organic Functional Group Preparations, Academic Press, vol. 1, Chapter 13 (1968); ditto, vol. 3, Chapter 10 (1972); and Japanese laid-open Patent Application No. H 2-171. After produced, compound [V] or a salt thereof can be used as a reaction mixture without isolation in the next process.

The amine compound or a salt thereof is commercially available, or it can be produced by processes known per se or any processes analogous therewith. Typical such processes are described in Survey of Organic Syntheses, Wiley-Interscience (1970), Chapter 8.

The guanidine derivative [I] or a salt thereof as produced by the production technology of the present invention has an excellent pesticidal activity as disclosed in Japanese Patent Application Kokai H 3-157308 and can be put to use in pesticidal compositions.

BEST MODE FOR CARRYING OUT OF THE INVENTION

The present invention is illustrated in further detail in the following examples, which do not limit the scope of the invention.

Proton NMR spectra were recorded with a Bruker AC-200P spectrometer using tetramethylsilane as an internal standard and all δ values were expressed in ppm. The pH value was measured using pH-test paper unless otherwise specified.

The abbreviations used in the following reference and working examples have the following meanings.

s: singlet, br: broad, d: doublet, t: triplet, m: multiplet, dd: doublet of doublets, J: coupling constant, Hz: Hertz, %: weight percent, m.p.: melting point, room temperature: ca 15–25° C.

REFERENCE EXAMPLE 1

To a mixture of O-methylisourea sulfate (5.00 g, 29.0 mmol) and 97% sulfuric acid (15.2 ml, 10 equivalents) was added 61% nitric acid (15.2 ml, 7 equivalents) dropwise at room temperature over 10 minutes. After one hour of stirring, the reaction mixture was poured on ice (100 g), neutralized with 40% aqueous sodium hydroxide solution, and extracted with ethyl acetate (300 ml). The extract was dried over anhydrous magnesium sulfate and concentrated under reduced pressure to provide 2.80 g (82.4% yield) of O-methyl-N-nitroisourea.

$^1$H-NMR (DMSO-d$_6$): 3.76 (3H, s), 8.60–9.20 (2H, br. s).

M.p. 107–109° C.

REFERENCE EXAMPLES 2 TO 5

The reaction procedure of Reference Example 1 was repeated under the conditions described below to provide O-methyl-N-nitroisourea.

TABLE 1

| Reference Example | Salt of O-methyl-isourea | Concentration of nitric acid (%) | Mol equivalent of nitric acid | Mol equivalent of sulfuric acid | Yield (%) |
|---|---|---|---|---|---|
| 1 | Sulfate | 61 | 7 | 10 | 82.4 |
| 2 | Sulfate | 67.5 | 7 | 10 | 88.2 |
| 3 | Sulfate | 98 | 3 | 5 | 91.2 |
| 4 | ½ Sulfate | 98 | 3 | 9 | 89.6 |
| 5 | Hydrochloride | 98 | 3 | 5 | 90.9 |

REFERENCE EXAMPLE 6

To a mixture of O-methylisourea sulfate (1031 g, 5.99 mol) and 97% sulfuric acid (940 ml, 3 equivalents) was added 98% nitric acid (760 ml, 3 equivalents) dropwise under ice-cooling over 2 hours. After 2 hours of stirring at room temperature, the reaction mixture was poured on ice (5000 g). The mixture was then cooled to −15° C. and allowed to stand for 0.5 hour at this temperature and the resulting crystals were collected by filtration. The crystals were suspended in water (1000 ml) and the suspension was adjusted to pH 8 with 40% aqueous sodium hydroxide solution (160 ml) and stirred at room temperature for 0.5 hour. The mixture was further stirred under ice-cooling for 0.5 hour and the resulting crystals were collected by filtration and dried. As a result, 542.7 g (76.1% yield) of O-methyl-N-nitroisourea was obtained.

REFERENCE EXAMPLE 7

To a mixture of O-methylisourea ½ sulfate (60.0 g, 0.49 mol) and 98% sulfuric acid (176.5 g, 1.76 mol) was added 98% fuming nitric acid (54.5 g, 0.85 mol, 1.7 equivalents) dropwise over 1 hour at 4–8° C. After 2.5 hours of srirring at 25° C., the reaction mixture was added to a mixture of ice (400 g) and water (440 ml). The mixture was then cooled to −12° C. and allowed to stand for 1.5 hours at this temperature and the resulting crystals were collected by filtration. The crystals were suspended in water (168 ml) and the suspension was adjusted to pH 8 with 30% aqueous sodium hydroxide solution (8.0 g) and stirred at 10° C. for 1 hour. The resulting crystals were collected by filtration and dried to provide 38.4 g (66.2% yield) of O-methyl-N-nitroisourea.

EXAMPLE 1

In dichloromethane (460 ml)—pyridine (92 g, 1.16 mol) was dissolved O-methyl-N-nitroisourea (46.2 g, 0.388 mol). This solution was cooled to −15° C. using an ice-methanol bath and phthaloyl chloride (95.0 g, 0.468 mol) was added dropwise over 10 minutes. After 2 hours of stirring, methanol (12.5 g) was added and the mixture was further stirred for 15 minutes. This reaction mixture was added to a mixture of concentrated hydrochloric acid (80 ml) and ice-water (400 ml), and the organic layer was taken and concentrated under reduced pressure. The crude product thus obtained was added to 200 ml of methanol and the mixture was stirred at room temperature for 30 minutes and under ice-cooling for 30 minutes. The resulting crystals were collected by filtration to provide 71.8 g (74.3% yield) of O-methyl-N-nitro-N'-phthaloylisourea.

$^1$H-NMR (CDCl$_3$): 4.15 (3H, s), 7.80–8.15 (4H, m).

m.p. 137–138.5° C.

EXAMPLE 2

In methanol (10 ml) was suspended O-methyl-N-nitro-N'-phthaloylisourea (2.00 g, 8.03 mmol) and, then, 5-(aminomethyl)-2-chlorothiazole (1.20 g, 8.07 mmol) was added dropwise over 15 minutes at 0° C. After 30 minutes of stirring at room temperature, the reaction mixture was diluted with water (20 ml) under ice-cooling and the resulting crystals were collected by filtration and dissolved in 10% aqueous sodium hydroxide solution (10 ml). This solution was stirred for 30 minutes and then adjusted to pH 4 with hydrochloric acid. The resulting crystals were collected by filtration and dried to provide 1.70 g (85.0% yield) of O-methyl-N-(2-chloro-5-thiazolylmethyl)-N'-nitroisourea.

$^1$H-NMR (DMSO-d$_6$): 3.87 (3H, s), 4.61 (2H, d, J=5.5 Hz), 7.61 (1H, s), 9.90 (1H, br. t, J=5.5 Hz).

m.p. 133–135° C.

EXAMPLE 3

Except that acetone was used as the reaction solvent, the reaction procedure of Example 2 was otherwise repeated to provide the object compound in a yield of 74.0%.

EXAMPLE 4

Except that acetonitrile was used as the reaction solvent, the reaction procedure of Example 2 was otherwise repeated to provide the object compound in a yield of 78.0%.

EXAMPLE 5

To a suspension of O-methyl-N-(2-chloro-5-thiazolylmethyl)-N'-nitroisourea (1.00 g, 4.00 mmol) in water (10 ml) was added 40% aqueous solution of methylamine (0.77 g; 9.92 mmol) dropwise. The mixture was stirred at room temperature for 14 hours and the resulting crystals were collected by filtration, washed with water (10 ml), and dried. As a result, 0.92 g (92.0% yield) of 1-(2-chloro-5-thiazolylmethyl)-3-methyl-2-nitroguanidine was obtained.

EXAMPLE 6

To a mixture of O-methyl-N-nitro-N'-phthaloylisourea (4.57 g, 18.3 mmol) and methanol (54 ml) was added 5-(aminomethyl)-2-chlorothiazole (2.96 g, 19.9 mmol) dropwise over 30 minutes under stirring at 3° C. After 1 hour of stirring at room temperature, the reaction mixture was poured in 50 g of iced water and the mixture was stirred for 10 minutes. The resulting crystals were collected by filtration and washed with water. The crystals were dissolved in 10% aqueous sodium hydroxide solution (60 ml) and the solution was stirred at room temperature for 0.5 hour. This solution was washed with chloroform (100 ml), brought to pH 4 with concentrated hydrochloric acid and the resulting crystals were collected by filtration. The crystals were washed with water. While a mixture of the above crystals and water (40 ml) was stirred at room temperature, 40% aqueous solution of methylamine (3.78 g, 48.8 mmol) was added. The mixture was stirred at room temperature for 1 hour and the resulting crystals were collected by filtration, washed with water, and dried to provide 2.56 g (56.0% yield) of 1-(2-chloro-5-thiazolylmethyl)-3-methyl-2-nitroguanidine.

M.p. 173.5–176.5° C.

EXAMPLE 7

To a mixture of O-methyl-N-nitro-N'-phthaloylisourea (2.90 g, 11.6 mmol) and dichloromethane (30 ml) was added a solution of 5-(aminomethyl)-2-chlorothiazole (1.90 g, 12.8 mmol) in dichloromethane (15 ml) dropwise over 25 minutes under constant stirring at 3° C. The mixture was further stirred at room temperature for 1 hour and the resulting crystals were separated by filtration and washed with 12 ml of dichloromethane. To the filtrate and washes combined was added water (30 ml) and while this mixture was stirred at room temperature, 40% aqueous solution of methylamine (1.89 g, 24.3 mmol) was added over 5 minutes. After 1 hour of stirring at room temperature, the resulting crystals were collected by filtration, washed with water, and dried to provide 2.15 g (74.0% yield) of 1-(2-chloro-5-thiazolylmethyl)-3-methyl-2-nitroguanidine.

EXAMPLE 8

To a mixture of O-methyl-N-nitro-N'-phthaloylisourea (2.89 g, 11.6 mmol) and water (20 ml) was added 5-(aminomethyl)-2-chlorothiazole (1.79 g, 12.0 mmol) en bloc under constant stirring at 3° C. The dropping funnel was washed with acetonitrile (1 ml) and the washes were added to the reaction mixture. After 2 hours of stirring at room temperature, 40% aqueous solution of methylamine (3.97 g, 5.11 mmol) was added and the mixture was stirred at room temperature for 40 minutes. The resulting crystals were collected by filtration and washed with water. The washed crystals were then stirred in acetonitrile (10 ml) for 15 minutes and then collected by filtration to provide 1.50 g (51.8% yield) of 1-(2-chloro-5-thiazolylmethyl)-3-methyl-2-nitroguanidine.

EXAMPLE 9

To a mixture of O-methyl-N-nitro-N'-phthaloylisourea (4.70 g, 18.9 mmol) and dichloromethane (25 ml) was added a solution of 5-(aminomethyl)-2-chlorothiazole (2.80 g, 18.9 mmol) in dichloromethane (2 ml) dropwise over 5 minutes under constant stirring at room temperature. After 30 minutes of stirring at room temperature, 75 ml of water was added to the reaction mixture and, then, 40% aqueous solution of methylamine (6.49 g, 83.6 mmol) was added over 2 minutes. The mixture was stirred at room temperature for 1.5 hours and the resulting crystals were collected by filtration, washed with water, and dried. As a result, 3.49 g (73.5% yield) of 1-(2-chloro-5-thiazolylmethyl)-3-methyl-2-nitroguanidine was obtained.

EXAMPLE 10

In a mixture of dichloromethane (10 ml) and water (15 ml) was suspended O-methyl-N-nitro-N'-phthaloylisourea (5.0 g, 19.46 mmol) and then, dichloromethane (5 ml) solution of 5-(aminomethyl)-2-chlorothiazole (3.25 g, 20.69 mmol, 1.06 equivalents) was added dropwise over 5 minutes under stirring at 10° C. After 30 minutes of stirring at room temperature, the reaction mixture was diluted with water (60 ml) and then, methylamine (6.7 ml, 77.84 mmol, 4.00 equivalents) was added. After 1.5 hours of stirring at room temperature, the resulting crystals were collected by filtration, washed with water and subsequently methanol. The washed crystals were dried to provide 3.83 g (78.8% yield) of 1-(2-chloro-5-thiazolylmethyl)-3-methyl-2-nitroguanidine as white crystals.

EXAMPLE 11

In a mixture of dichloromethane (10 ml) and water (15 ml) was suspended O-methyl-N-nitro-N'-phthaloylisourea (5.0 g, 20.0 mmol) and then, dichloromethane (5 ml) solution of 5-(aminomethyl)-2-chloropyridine (3.0 g, 21.0 mmol, 1.05 equivalents) was added dropwise over 5 minutes under stirring at 10° C. After 30 minutes of stirring at room temperature, the reaction mixture was diluted with water (60 ml) and then, methylamine (6.7 ml, 77.84 mmol, 4.0 equivalents) was added. After 1.5 hours of stirring at room temperature, 30 ml of 20% aqueous sodium hydroxide solution was added to separate a water phase from an organic phase. The water phase was washed with dichloromethane, neutralized with concentrated hydrochloric acid, and adjusted to pH 3.0. The resulting crystals were collected by filtration, washed with water and subsequently methanol. The washed crystals were dried to provide 3.12 g (64.0% yield) of 1-(6-chloro-3-pyridylmethyl)-3-methyl-2-nitroguanidine as white crystals. M.p. 159–160° C.

$^1$H-NMR (DMSO-$d_6$) δ: 2.85 (3H, d, J=4.4 Hz), 4.44 (2H, d, J=6.0 Hz), 7.49 (1H, d, J=8.2 Hz), 7.80 (1H, dd, J=8.2 Hz, 2.6 Hz), 7.90 (1H, br), 8.37 (1H, d, J=2.6 Hz), 9.10 (1H, br).

IR(nujol): 3300, 1620, 1570, 1380, 1341, 1240 (cm$^{-1}$).

EXAMPLE 12

To a suspension of O-methyl-N-(2-chloro-5-thiazolylmethyl)-N'-nitroisourea (87% purity, 47.2 g, 0.164 mol) in water (410 ml) was added 40% aqueous solution of methylamine (25.5 g, 0.328 mol, 2.0 equivalents) dropwise at 23° C. After 2 hours of stirring at room temperature, the mixture was allowed to stand under ice-cooling and then, 36% hydrochloric acid (14.3 mol, 0.168 mol) was added dropwise at 13–20° C. The resulting crystals were collected by filtration to provide 39.1 g (95.6% yield) of 1-(2-chloro-5-thiazolylmethyl)-3-methyl-2-nitroguanidine.

EXAMPLE 13

To a mixture of O-methyl-N-nitroisourea (3.0 g, 0.0252 mol), 36% hydrochloric acid (2.2 ml), and water (50 ml) was added 5-aminomethyl-2-chlorothiazole (93% purity, 4.4 g, 0.0275 mol) at 20° C. This mixture was stirred at room temperature for 6 hours and then extracted with dichloromethane. The extract was dried over anhydrous magnesium sulfate and concentrated to provide 3.5 g (55.4% yield) of O-methyl-N-(2-chloro-5-thiazolylmethyl)-N'-nitroisourea.

$^1$H-NMR (DMSO-$d_6$): 3.87 (3H, s), 4.61 (2H, d, J=5.5 Hz), 7.61 (1H, s), 9.90 (1H, br. t, J=5.5 Hz).

EXAMPLE 14

To a mixture of O-methyl-N-nitroisourea (2.0 g, 0.0168 mol), 36% hydrochloric acid (1.5 ml), sodium chloride (8.0 g), and water (40 ml) was added 5-aminomethyl-2-chlorothiazole (2.5 g, 0.0168 mol) at 20° C. This mixture was adjusted to pH 7 with 30% aqueous solution of sodium hydroxide and stirred at room temperature for 8 hours, after which it was extracted with dichloromethane. The extract was dried over anhydrous magnesium sulfate and concentrated to provide 2.7 g (64.1% yield) of O-methyl-N-(2-chloro-5-thiazolylmethyl)-N'-nitroisourea.

M.p. 133–135° C.

EXAMPLE 15

To a mixture of O-methyl-N-nitroisourea (2.0 g, 0.0168 mol), 36% hydrochloric acid (1.5 ml), sodium chloride (8.0 g), and water (40 ml) was added 5-aminomethyl-2-chlorothiazole (2.5 g, 0.0168 mol) at 20° C. This mixture was adjusted to pH 7 with 30% aqueous solution of sodium hydroxide and stirred at room temperature for 13 hours. Then, 40% aqueous solution of methylamine (4.4 ml, 0.0511 mol) was added and the mixture was stirred at room temperature for 2 hours. The resulting crystals were collected by filtration, washed with water, and dried to provide 1.54 g (36.7% yield) of 1-(2-chloro-5-thiazolylmethyl)-3-methyl-2-nitroguanidine.

EXAMPLE 16

O-methyl-N-nitroisourea (3.0 g, 0.0252 mol), acetic acid (1.5 ml, 0.0262 mol, 10.4 equivalents), and 5-(aminomethyl)-2-chlorothiazole (93% purity, 4.4 g, 0.0275 mol, 1.09 equivalents) were added to water (55 ml) in this order at 24° C. The reaction mixture was adjusted to pH 7 with 30% aqueous sodium hydroxide solution. The mixture was stirred at room temperature for 2 hours and then extracted with dichloromethane. The extract was dried over anhydrous magnesium sulfate and concentrated under reduced pressure to provide 2.9 g (46.0% yield) of O-methyl-N-(2-chloro-5-thiazolylmethyl)-N'-nitroisourea.

EXAMPLE 17

Except that 67.5% nitric acid (1.7 ml, 0.0257 mol, 1.02 equivalents) was used instead of acetic acid, the reaction procedure of Example 16 was repeated to provide 3.4 g (54.0% yield) of O-methyl-N-(2-chloro-5-thiazolylmethyl)-N'-nitroisourea.

EXAMPLE 18

Except that 97% sulfuric acid (0.7 ml, 0.0127 mol, 0.5 equivalents) was used instead of acetic acid, the reaction procedure of Example 16 was repeated to provide 2.9 g (46.0% yield) of O-methyl-N-(2-chloro-5-thiazolylmethyl)-N'-nitroisourea.

EXAMPLE 19

O-methyl-N-nitroisourea (1.2 g, 0.01 mol) was added to water (30 ml) dissolving sodium chloride (4.7 g). Then, 70% perchloric acid (1.52 g, 0.0106 mol, 1.06 equivalents) was added, and 5-(aminomethyl)-2-chlorothiazole (1.49 g, 0.01 mol, 1.00 equivalent) was added at 24° C. The mixture was adjusted to pH 7 with 30% aqueous sodium hydroxide solution. After 24 hours of stirring at room temperature, the resulting crystals were collected by filtration to provide 1.56 g (62.2% yield) of O-methyl-N-(2-chloro-5-thiazolylmethyl)-N'-nitroisourea.

EXAMPLE 20

5-(Aminomethyl)-2-chlorothiazole (7.43 g, 50.0 mmol) was dissolved in water (96 ml), and 47% hydrobromic acid (5.78 ml 50.0 mmol) was added. The pH was 3.4 at this time. To this reaction mixture was added O-methyl-N-nitroisourea (7.19 g, 60.0 mmol) and sodium chloride (17.5 g, 0.30 mol), and adjusted to pH 6.2 with aqueous sodium hydroxide solution (0.5 N) using pH meter. After 24 hours of stirring at room temperature, the resulting white crystals were collected by filtration under reduced pressure, and washed with water. The washed crystals were dried under reduced pressure (80° C., 2 hours) to provide 8.7 g (69.4% yield) of O-methyl-N-(2-chloro-5-thiazolylmethyl)-N'-nitroisourea.

EXAMPLE 21

O-methyl-N-nitroisourea (2.0 g, 0.0168 mol) was added to water (40 ml) dissolving calcium chloride dihydrate (8.0 g). Then, 36% hydrochloric acid (1.5 ml, 0.0176 mol, 1.05 equivalents) was added, and 5-(aminomethyl)-2-chlorothiazole (2.5 g, 0.0168 mol, 1.00 equivalent) was added at 24° C. The mixture was adjusted to pH 7 with 30% aqueous sodium hydroxide solution. After 19 hours of stirring at room temperature, the resulting crystals were collected by filtration to provide 2.48 g (59.1% yield) of O-methyl-N-(2-chloro-5-thiazolylmethyl)-N'-nitroisourea.

EXAMPLE 22

To an aqueous solution (40 ml) of sodium chloride (7.9 g, 0.13 mol) were added O-methyl-N-nitroisourea (2.3 g, 19.3 mmol), concentrated hydrochloric acid (1.49 ml, 16.8 mmol) and 5-(aminomethyl)-2-chlorothiazole (2.5 g, 16.8 mmol). The mixture was adjusted to pH 7.0 with 30% aqueous sodium hydroxide solution, and stirred at room temperature for 3 days. The resulting white crystals were collected by filtration under reduced pressure, and washed with water. The washed crystals were dried under reduced pressure (80° C., 2 hours) to provide 3.23 g (76.6% yield) of O-methyl-N-(2-chloro-5-thiazolylmethyl)-N'-nitroisourea.

EXAMPLE 23

5-(Aminomethyl)-2-chlorothiazole (7.43 g, 50.0 mmol) was dissolved in water (96 ml), and concentrated hydrochloric acid (4.22 ml, 50.0 mmol) was added. To this reaction mixture was added O-methyl-N-nitroisourea (7.19 g, 60.0 mmol), and adjusted to pH 6.7 with aqueous sodium hydroxide solution (0.5 N) using PH meter. After 20 hours of stirring at room temperature, maintaining pH 6.7, the resulting white crystals were collecte by filtration under reduced pressure, and washed with water. The washed crystals were dried under reduced pressure (80° C., 2 hours) to provide 7.85 g, (62.6% yield) of O-methyl-N-(2-chloro-5-thiazolylmethyl)-N'-nitroisourea.

EXAMPLE 24

5-(Aminomethyl)-2-chlorothiazole (1.49 g, 10.0 mmol) was dissolved in diluted hydrochloric acid (15 ml, 10.0 mmol), and O-methyl-N-nitroisourea (1.31 g, 11.0 mmol) was added. The pH was 2.1 at this time. This reaction mixture was adjusted to pH 6.2 with aqueous sodium hydroxide solution (0.1 N, 4 ml, 0.40 mmol) using pH meter. Water (1 ml) was added to increase the whole volume to 20 ml. After 16 hours of stirring at room temperature (pH was 7.1 at this time), the resulting white crystals were collected by filtration under reduced pressure, and washed with water. The washed crystals were dried under reduced pressure (80° C., 2 hours) to provide 1.62 g (64.6% yield) of O-methyl-N-(2-chloro-5-thiazolylmethyl)-N'-nitroisourea.

EXAMPLE 25

5-(Aminomethyl)-2-chlorothiazole (1.49 g, 10.0 mmol) was dissolved in diluted hydrochloric acid (15 ml, 10.0 mmol), and O-methyl-N-nitroisourea (1.31 g, 11.0 mmol) and sodium chloride (1.17 g, 20.0 mmol) were added. pH was 2.1 at this time. This reaction mixture was adjusted to pH 6.2 with aqueous sodium hydroxide solution (0.1 N, 3.8 ml, 0.38 mmol) using pH meter. Water (1.2 ml) was added to increase the whole volume to 20 ml. After 16 hours of stirring at room temperature (pH was 6.8 at this time), the resulting white crystals were collected by filtration under reduced pressure, and washed with water. The washed crystals were dried under reduced pressure (80° C., 2 hours) to provide 1.72 g (68.6% yield) of O-methyl-N-(2-chloro-5-thiazolylmethyl)-N'-nitroisourea.

EXAMPLE 26

5-(Aminomethyl)-2-chlorothiazole (1.49 g, 10.0 mmol), was dissolved in diluted hydrochloric acid (15 ml, 10.0 mmol), and O-methyl-N-nitroisourea (1.31 g, 11.0 mmol) and sodium chloride (4.68 g, 80.0 mmol) were added. The pH was 1.9 at this time. This reaction mixture was adjusted to pH 6.2 with aqueous sodium hydroxide solution (0.1 N, 5.0 ml, 0.50 mmol) using pH meter. After 16 hours of stirring at room temperature (pH was 6.7 at this time), the resulting white crystals were collected by filtration under reduced pressure, and washed with water. The washed crystals were dried under reduced pressure (80° C., 2 hours) to provide 1.74 g (69.4% yield) of O-methyl-N-(2-chloro-5-thiazolylmethyl)-N'-nitroisourea.

EXAMPLE 27

5-(Aminomethyl)-2-chlorothiazole (7.43 g, 50.0 mmol) was dissolved in water (96 ml), and concentrated hydrochloric acid (4.22 ml, 50.0 mmol) was added. To this reaction mixture was added O-methyl-N-nitroisourea (6.25 g, 52.5 mmol) and chloroform (30 ml), and adjusted to pH 6.7 with aqueous sodium hydroxide solution (0.5 N) using pH meter. After 24 hours of stirring at room temperature, maintaining pH 6.7, the organic phase was separated from the water phase. The water phase was extracted with chloroform (100 ml), and the combined organic phase was concentrated under reduced. Water (50 ml) was added to the residue to stir for a while. The resulting crystals were collected by filtration under reduced pressure, and washed with water. The washed crystals were dried under reduced pressure (80° C., 2 hours) to provide 7.80 g (62.2% yield) of O-methyl-N-(2-chloro-5-thiazolylmethyl)-N'-nitroisourea.

EXAMPLE 28

To an aqueous solution (31 ml) of sodium chloride (6.1 g, 0.10 mol) and O-methyl-N-nitroisourea (1.5 g, 12.9 mmol) was added 5-(aminomethyl)-2-chlorothiazole hydrochloride (2.4 g, 12.5 mmol). The reaction mixture was adjusted to pH 7.0 with aqueous sodium hydroxide solution, and stirred at room temperature for 4 hours. The resulting white crystals were collected by filtration under reduced pressure, and washed with water. The washed crystals were dried under reduced pressure (80° C., 2 hours) to provide 1.92 g (60.8% yield) of O-methyl-N-(2-chloro-5-thiazolylmethyl)-N'-nitroisourea.

EXAMPLE 29

To a mixture of O-methyl-N-nitroisourea (1.25 g, 10.53 mmol), water (20 ml) and concentrated hydrochloric acid (0.85 ml, 10.03 mmol) was added 5-(aminomethyl)-2-chloropyridine (1.43 g, 10.03 mmol) dropwise over 5 minutes at room temperature with stirring. The reaction mixture was neutralized with 40% aqueous sodium hydroxide solution and adjusted to pH 7.2. After 17 hours of stirring at room temperature, the resulting crystals were collected. The crystals were washed with water and dried. As a result, 1.16 g (47.3% yield) of O-methyl-N-(6-chloro-3-pyridylmethyl)-N'-nitroisourea was obtained as white crystals. M.p. 112–113° C.

$^1$H-NMR (CDCl$_3$) δ: 3.98 (3H, s), 4.57 (2H, d, J=6.0 Hz), 7.38 (1H, d, J=8.2 Hz), 7.63 (1H, dd, J=8.2 Hz, 2.4 Hz), 8.36 (1H, d, J=2.4 Hz), 9.43 (1H, br). IR (nujol): 3250, 1590, 1520, 1390, 1240, 1210 (cm$^{-1}$).

EXAMPLE 30

To a mixture of O-methyl-N-(6-chloro-3-pyridylmethyl)-N'-nitroisourea (970 mg, 3.96 mmol) and water (30 ml) was added 40% aqueous solution of methylamine (0.7 ml, 7.92 mmol, 2.0 equivalents) at room temperature with stirring. After 1.5 hours of stirring at room temperature, the resulting crystals were collected. The crystals were washed with water and methanol, and dried. As a result, 860 mg (89.1% yield) of 1-(6-chloro-3-pyridylmethyl)-3-methyl-2-nitroguanidine.

Industrial Applicability

According to the production of the present invention using the compound [II] and/or the novel compound [IV], the guanidine derivative [I] or a salt thereof having excellent pesticidal activity can be produced advantageously on a commercial scale.

We claim:
1. A process for producing a compound of the forumula:

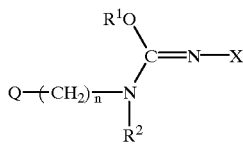

[VI]

wherein R$^1$ is a hydrocarbon group which is substituted or unsubstituted, R$^2$ is H or a hydrocarbon group which is substituted or unsubstituted, Q is a heterocyclic group which is substituted or unsubstituted, X is an electron attracting group, and n is 0 or 1, or a salt thereof, which comprises (A) reacting a compound of the formula:

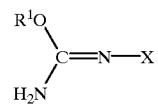

[II]

wherein the symbols are as defined above, or a salt thereof, with a compound of the formula:

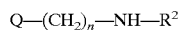

[V]

wherein the symbols are as defined above, or a salt thereof, or (B) reacting a compound of the formula (II) or a salt thereof, with a compound of the formula:

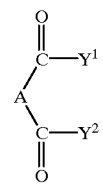

[III]

wherein A is a divalent hydrocarbon group which is substituted or unsubstituted, and Y$^1$ and Y$^2$ are the same or different leaving group, and further reacting the resultant compound of the formula:

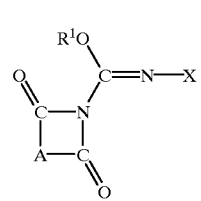

[IV]

wherein the symbols are as defined above, with the compound of the formula (V) or a salt thereof.

2. A process according to claim 1, wherein R$^1$ is a C$_{1-3}$ alkyl group.

3. A process according to claim 1, wherein X is nitro.

4. A process according to claim 1, wherein R$^2$ is H or a C$_{1-4}$ alkyl group.

5. A process according to claim 1, wherein Q is a 5- or 6-membered aromatic heterocyclic group, having at least one nitrogen atom or sulfur atom, which is unhalogenated or halogenated.

6. A process according to claim 1, wherein n is 1.

7. A process according to claim 1, wherein the reaction in process (A) is performed, and is conducted in water or in a mixture of water and an organic solvent.

8. A process according to claim 1, wherein the reaction in process (A) is performed, and is conducted in the range of about pH 5 to pH 8.

9. A process for producing the compound (VI) or a salt thereof

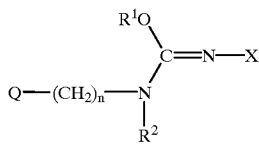

wherein $R^1$ is a hydrocarbon group which is substituted or unsubstituted, $R^2$ is H or a hydrocarbon group which is substituted or unsubstituted, Q is a heterocyclic group which is substituted or unsubstituted, X is an electron attracting group, and n is 0 or 1, which comprises reacting a compound (IV)

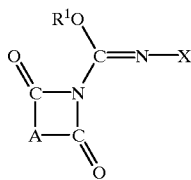

wherein A is a divalent hydrocarbon group which is substituted or unsubstituted, with a compound (V)

$$Q\text{---}(CH_2)_n\text{---}NH\text{---}R^2 \quad (V)$$

or a salt thereof.

10. A process for producing O-methyl-N-(6-chloro-3-pyridylmethyl)-N'-nitroisourea or a salt thereof, which comprises reacting O-methyl-N-nitroisourea or a salt thereof with 5-(aminomethyl)-2-chloropyridine or a salt thereof.

11. A process for producing O-methyl-N-(2-chloro-5-thiazolylmethyl)-N'-nitroisourea or a salt thereof, which comprises reacting O-methyl-N-nitroisourea or a salt thereof with 5-(aminomethyl)-2-chlorothiazole or a salt thereof.

12. A process according to claim 1, wherein method (A) is used.

13. A process according to claim 1 wherein method (B) is used.

* * * * *